United States Patent

Van Der Weegen

[11] Patent Number: 5,722,983
[45] Date of Patent: Mar. 3, 1998

[54] DILATING SPECULUM

[76] Inventor: Clemens Van Der Weegen, 15 Churchill Avenue, Strathfield, New South Wales 2135, Australia

[21] Appl. No.: 522,275
[22] PCT Filed: Mar. 9, 1994
[86] PCT No.: PCT/AU94/00111
§ 371 Date: Nov. 30, 1995
§ 102(e) Date: Nov. 30, 1995
[87] PCT Pub. No.: WO94/21160
PCT Pub. Date: Sep. 29, 1994

[30] Foreign Application Priority Data

Mar. 15, 1993 [AU] Australia ............... PL7802

[51] Int. Cl.[6] ............................... A61M 29/00
[52] U.S. Cl. ................................... 606/193
[58] Field of Search ................... 600/115, 116, 600/207, 208; 606/191, 194, 195, 192, 193, 197, 198; 604/96

[56] References Cited

U.S. PATENT DOCUMENTS

Re. 35,312  8/1996  Christoudias ............... 600/207
4,198,981   4/1980  Sinnreich .................... 606/193
5,176,697   1/1993  Hasson et al. ............... 606/191
5,338,297   8/1994  Kowr et al. .................. 606/193

Primary Examiner—Michael Buiz
Assistant Examiner—William Lewis
Attorney, Agent, or Firm—James Ray & Ass.

[57] ABSTRACT

A dilating speculum comprises a tubular body (8) adapted for connection at one end to an eye-piece and light source, a tubular probes (11) adapted to be inserted into the vagina or other body cavity and comprising an outer probe part (13) detachably secured to the tubular body (8) and an inner probe part (12) lodged within the bore of the outer part (13). An inflatable latex (15) sheath surrounds a length of the probe (11) and is sealed thereto at each end of that length. The seal at one end is effected by virtue of an end portion of the sheath (15) being sandwiched between the two probe parts (12, 13) and at the other end by a stretched elastic ring (35) encircling the probe (11) and sheath (15). A passage (24, 23, 25, 28, 29) through the body (8) and probe (11) allows the sheath (15) to be inflated between the seals.

8 Claims, 4 Drawing Sheets

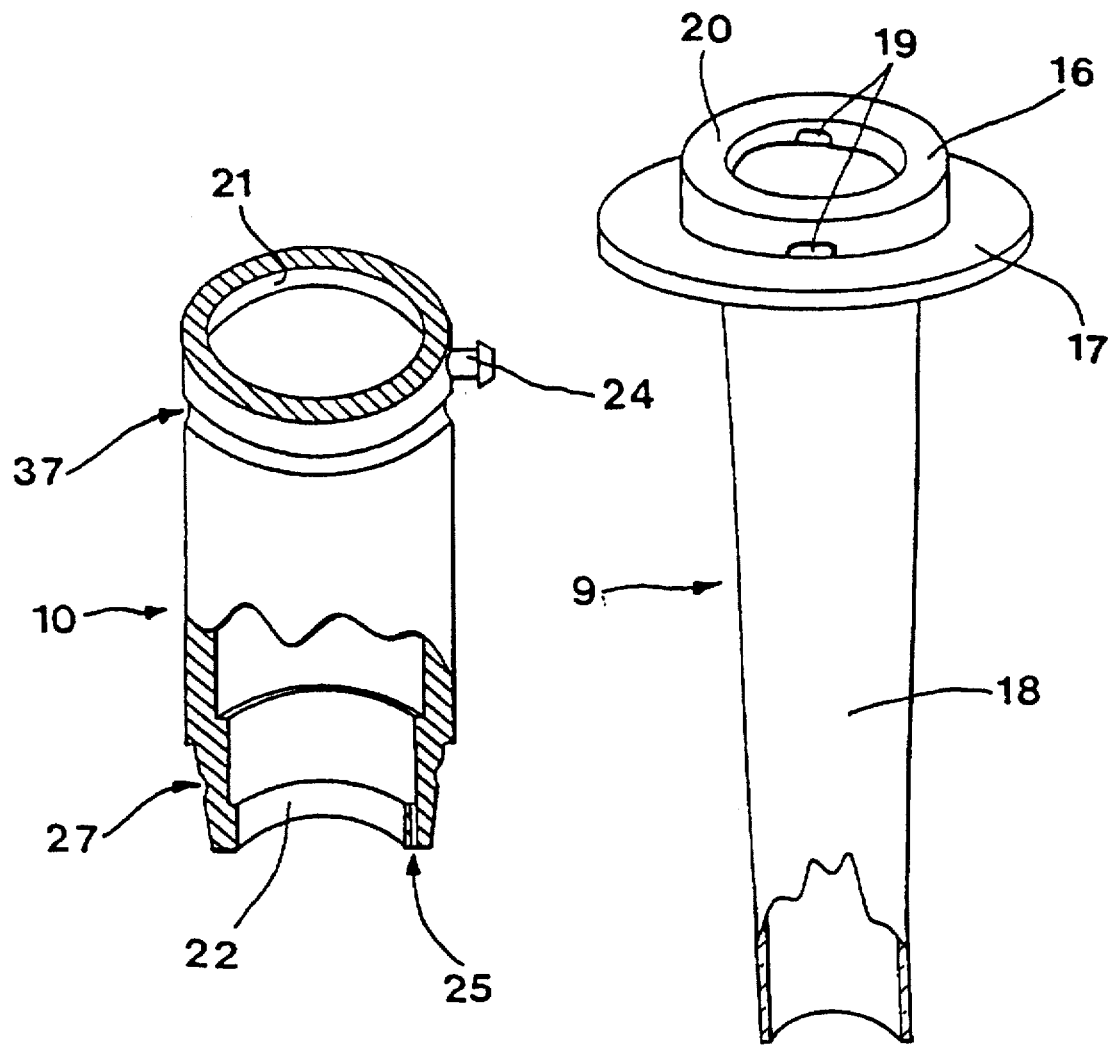

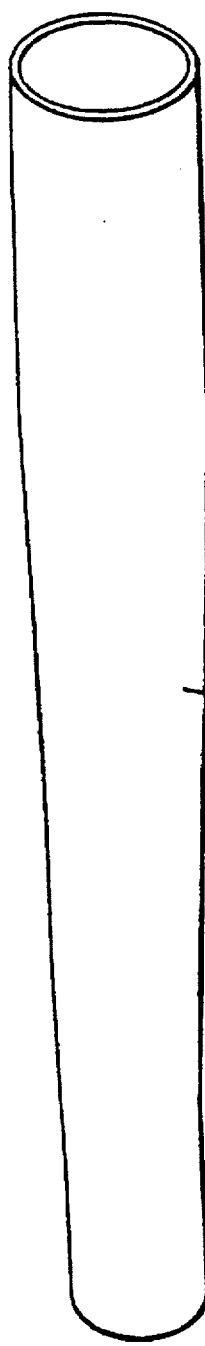
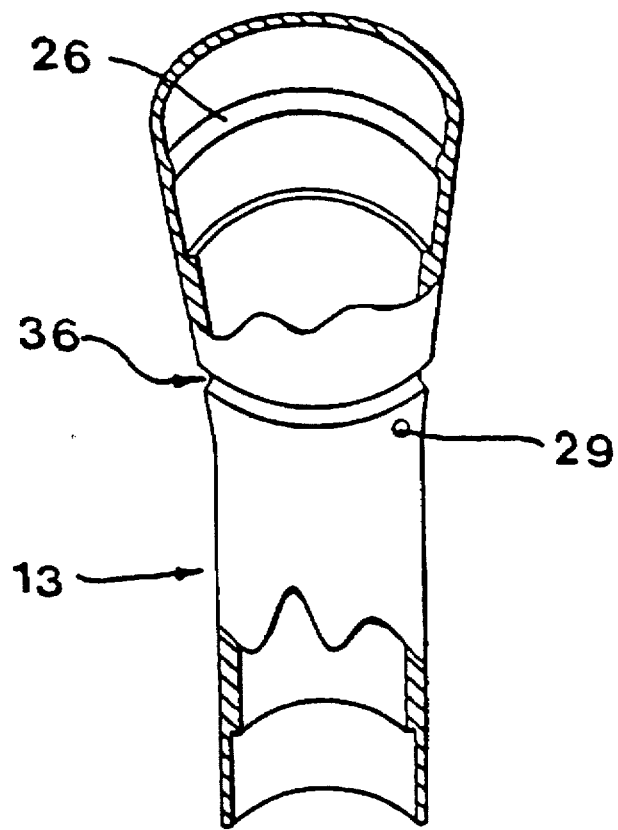
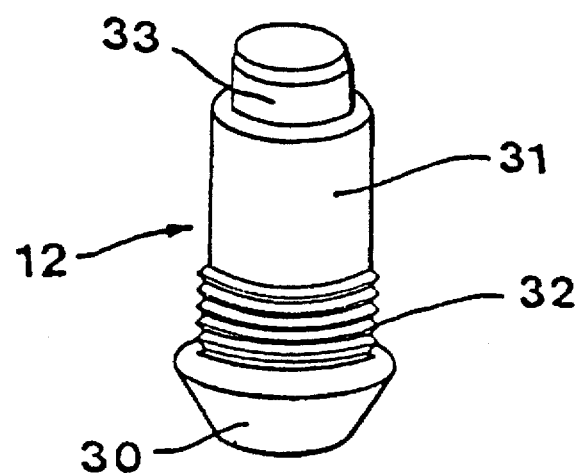
FIG 5
FIG 6
FIG 7

DILATING SPECULUM

TECHNICAL FIELD

This invention relates to dilating speculums, that is to say surgical instruments of various forms used for dilating body cavities and/or the orifices thereof so as to facilitate examinations of, or operations within, the interior of the cavity.

BACKGROUND ART

Generally speaking, there are two types of speculums in common use, namely those that do not substantially dilate the body cavity and those that do.

Non-dilating speculums are relatively simple tubular devices, frequently made of transparent plastics material, frequently fitted with an eye-piece including a light source, which are inserted into the body cavity to enable it to be inspected. Sometimes that part of the speculum that enters the body cavity is a detachable, single use, disposable item.

Prior known dilating speculums have comprised a tubular array of two or more rigid, elongate leaves, frequently of arcuate cross-section, and means to expand the array by bodily, generally radially outwardly, movement of the individual leaves.

It is usual, because of the need for strength, for dilating speculums to be made of metal. This has precluded the use of disposable, single use components in such speculums, rendering it necessary for dilating speculums to be thoroughly cleaned and sterilised after each use.

DISCLOSURE OF INVENTION

Quite often it is desirable or necessary for the inspection to be performed on a conscious and alert patient, and almost invariably this causes discomfort at least, and in many instances considerable pain. This is particularly so when relatively simple dilating speculums comprising only two separable leaves are used.

Furthermore, the insertion of metallic objects into body orifices, and the cold sensation created thereby, is psychologically distressing to many patients. So much so that some women put themselves at risk by failing to have routine vaginal examinations as a check on possible cervical cancer, for example, so called pap smears, merely because of their repugnance to the use of prior known metallic dilating speculums.

Attempts to alleviate the unpleasantness associated with the use of simple prior known dilating speculums have resulted in speculums having more than two leaves. This reduces the pressure between the speculum and the surface of the dilated cavity, but introduces still further undesirable complexity into the mechanism with consequent high cost, and of course does nothing to alleviate the disadvantage of metallic speculums indicated above.

An object of the invention is to provide a dilating speculum that at least alleviates the unpleasantness associated with the use of known speculums of that type.

A further object of the invention, at least in respect of its preferred embodiments, is to provide a dilating speculum having the single use, disposable facilities of prior known non-dilating speculums.

The invention achieves that object by providing a dilating speculum in which the dilation of the cavity is effected by inflating a substantially transparent balloon within the cavity in question. This ensures, for any given degree of dilation, maximum area of contact between the speculum and the cavity walls and therefore minimum pressure therebetween. It also ensures that the speculum moulds itself to the particular configuration of the patient. It avoids the cold sensation associated with the use of metal speculums.

The invention consists in a speculum, for use in examining the interior of a body cavity, comprising a tubular body having two ends, a tubular probe adapted to enter said body cavity detachably secured to said tubular body so as to project beyond one of the ends thereof, an inflatable element encircling said probe, and means to inflate said element.

The inflatable element may be an annular balloon, that is to say a component akin to a miniature inner tube for a pneumatic tire, encircling the probe intermediate its ends. It may be in the nature of a transparent spherical balloon enclosing the tip and a part of the length of the probe. However for preference the inflatable element is in the form of a sheath of latex or other thin film covering a length of the probe and sealed to the probe at each end of that length. In this event the element is inflated by admitting gas into the space between the sheath and that length of the probe.

In preferred embodiments the other end of the tubular body is fashioned to receive a conventional eye-piece and light source, as used in prior known non-dilating speculums, or may permanently incorporate same.

In other preferred embodiments, the speculum may further comprise a removable tubular liner, extending through the bore of the speculum body, and, preferably into the bore of the probe, whereby fluids, instruments, such as tissue collecting spatulas, or other items may be passed without contacting the speculum's tubular body.

BRIEF DESCRIPTION OF DRAWINGS

By way of example, an embodiment of the above described invention is described in more detail hereinafter with reference to the accompanying drawings.

FIG. 3 is a partly cut away perspective view of an inner body o part of the speculum of FIG. 1.

FIG. 4 is a view similar to FIG. 3 of an outer body part of the speculum of FIG. 1.

FIG. 5 is a perspective view of a tubular liner, being a component of the speculum of FIG. 1.

FIG. 6 is a view similar to FIG. 3 of an outer probe part of the speculum of FIG. 1.

FIG. 7 is a view similar to FIG. 3 of an inner probe part of the speculum of FIG. 1.

BEST MODE OF CARRYING OUT THE INVENTION

Figure 1:
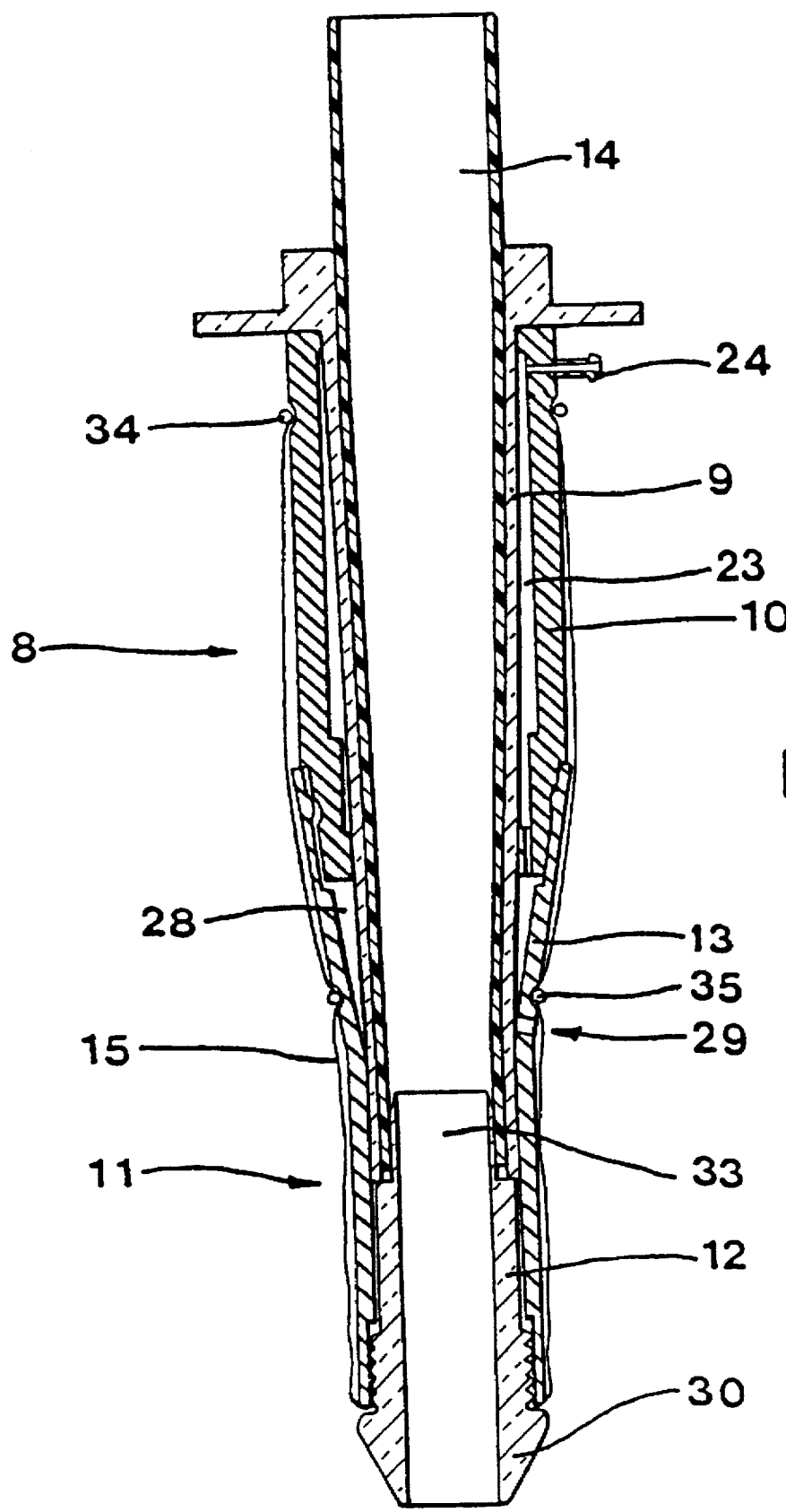
FIG. 1 is a longitudinal section of a dilating speculum according to the invention with its inflatable element deflated, ready for insertion into a body cavity.

The illustrated speculum is intended for use in the examination of the vagina. It comprises a tubular body 8, comprising an inner body part 9 and an outer body part 10, a tubular probe 11, comprising an inner probe part 12 and an outer probe part 13, a tubular liner 14, and an inflatable sheath 15.

The inner body part 9 is a colourless, transparent plastics moulding comprising an annular head 16, a shielding flange 17 and a slightly tapered elongated spigot 18. The head 16 is recessed at 19 to enable it to be engaged by a conventional unit comprising an eye-piece and light-source with handle, whereby the speculum as a whole may be manipulated while the rear face 20 of the head 16 is brightly illuminated and the operator is looking into and along the bore of the spigot 18. A suitable unit of that kind is currently marketed in many countries by the firm Heine Optotechnik under that firm's trade mark UniSpec.

As the inner body part 9 is transparent the light falling on the face 20 is transmitted along the spigot 18, as is the light entering the upper end of the spigot's bore. That term "upper" and others of like positional intent are used herein with reference to the speculum as oriented in the drawings.

The outer body part 10 is also a plastics moulding. It is not necessarily transparent, but may with advantage be so. It comprises a tubular barrel encircling the upper part of the spigot 18. It fits tightly against the outer surface of the spigot 18 at an upper sealing surface 21 and at a lower sealing surface 22. The inner surface of the outer body part 10 and the outer surface of the spigot 9 are spaced apart slightly between the two sealing surfaces 21 and 22, to provide a first airway 23 (FIGS. 1 and 2) extending from an air supply nipple 24 to a transfer port 25. The nipple 24 is adapted to enter the bore of a flexible air supply tube (not shown) extending to a manually operable dilation bulb or other air supply means, whereby air may be pumped into the airway 23.

The body 8 preferably comprises two parts as described above primarily for ease of manufacture, there is no reason fundamental to the invention preventing a one piece body being used.

The outer probe part 11 is detachably securable to the lower end of the outer body part 10. It also is a preferably transparent plastics o moulding. It may simply snap onto the body part 10, and to that end it may be provided with an internal rib 26 adapted to snap engage within a mating groove 27 in the outer body part 10. It comprises a tapered upper part and a parallel walled or very slightly tapered lower part. The lower part is adapted to snugly receive the lower end of the body spigot 18, whereas the upper part is spaced therefrom to define a second airway 28 extending from the transfer port 25 to an outlet port 29 piercing the wall of the outer probe part 13.

The inner probe part 12 is also a tubular, colourless, transparent plastics moulding. It comprises a smooth, externally tapered head 30 adapted to abut the bottom end face of the outer probe part 13, a parallel sided shank 31 adapted to enter the bore of the outer probe part 13 with a small but detectable clearance therebetween, a ribbed sealing formation 32 adapted to neatly engage a co-acting sealing zone at the bottom end of the bore of the outer probe part 13, and a sharp edged upwardly projecting spigot 33. The purpose of these respective formations will become clear from the following description, it suffices at the moment to say that the inner probe part 12 is frictionally retained firmly in the outer probe part 13.

Being transparent, the inner probe part 12 conducts light from the inner body part 9 and emits same through its tapered end face.

The probe 11 is sized and shaped as a whole to enable it to be comfortably inserted into and removed from the vagina.

The liner 14 is a preferably dark coloured, opaque, slightly tapered tube. It is a neat fit within the bores of the inner body part 9 and the outer probe part 13 and about the spigot 33.

The sheath 15 is in the nature of a conventional condom, that is to say, before assembly into the speculum as described hereinafter, it is a thin walled latex tube closed at one end and with a circumferential bead 34 at its other, open end. In this event, the sheath may be assembled to the probe as follows. The outer probe part 13 is inserted into the open end of the sheath until the bottom end of the outer probe part 13 reaches the closed end of the sheath. Then the inner probe part 12 may be thrust into the outer probe part 13, to carry a part of the closed end of the sheath with it into the bore of the outer probe part 13, until the inner probe part 12 is fully homed. This results in an end part of the sheath becoming sandwiched between the two probe parts, where it is held and sealed to the probe near the bottom end thereof by the sealing ribs 32. Usually the sharp edge on the spigot 33 will cause the closed end of the sheath, as supplied, to rupture so as to leave the bore of the speculum clear of obstruction. If this does not happen, and a part of the sheath remains as a stretched diaphragm across the upper end of the spigot 33, it is a simple matter to insert a sharp pointed rod or the like into the bottom end of the speculum to rupture that diaphragm.

The sheath is then further sealed to the probe 11 by emplacing a sealing element, such as a stretched elastomeric O-ring 35, about the sheath 15 in a groove 36 provided in the outer surface of the outer probe part 13 and positioned so as to locate the sealing element above the outlet port 29.

The foregoing assembly of the sheath 15 to the probe 11 may be effected under sterile conditions in a factory or the like, for supply, with the liner 14, in a sterile package for use by a medical practitioner at the time of inspection. The speculum may then be set up for use by the practitioner simply by fitting the outer probe part 13 onto the body 8, and then rolling the skirt of the sheath up over the outside of the body 8 until the bead 34 is lodged correctly in a groove 37 provided in the outer surface of the body at a point well above any part likely to be rendered non-sterile during use of the speculum, or, more importantly, if non-sterile, likely to infect the woman being examined during the examination, thereby to ensure that an uninflated skirt of the sheath covers all such parts. The practitioner may then insert the liner 14 until it overlaps the spigot 33, as shown in the drawings, which ensures that the bore of the reusable body 8 is fully protected from contamination during the use of the speculum.

The sheath 15 is made from a latex or other elastomeric film of the kind used for condoms. On the other hand, in other embodiments, it may be made from a somewhat thicker, preferably transparent plastics film. In any event, it is preferably stretchable and sized so that in its deflated condition it moulds itself smoothly against the outside surface of the speculum. This facilitates the insertion of the speculum with the sheath deflated, however a non-extensible, loose fitting sheath is also useable.

Figure 2:
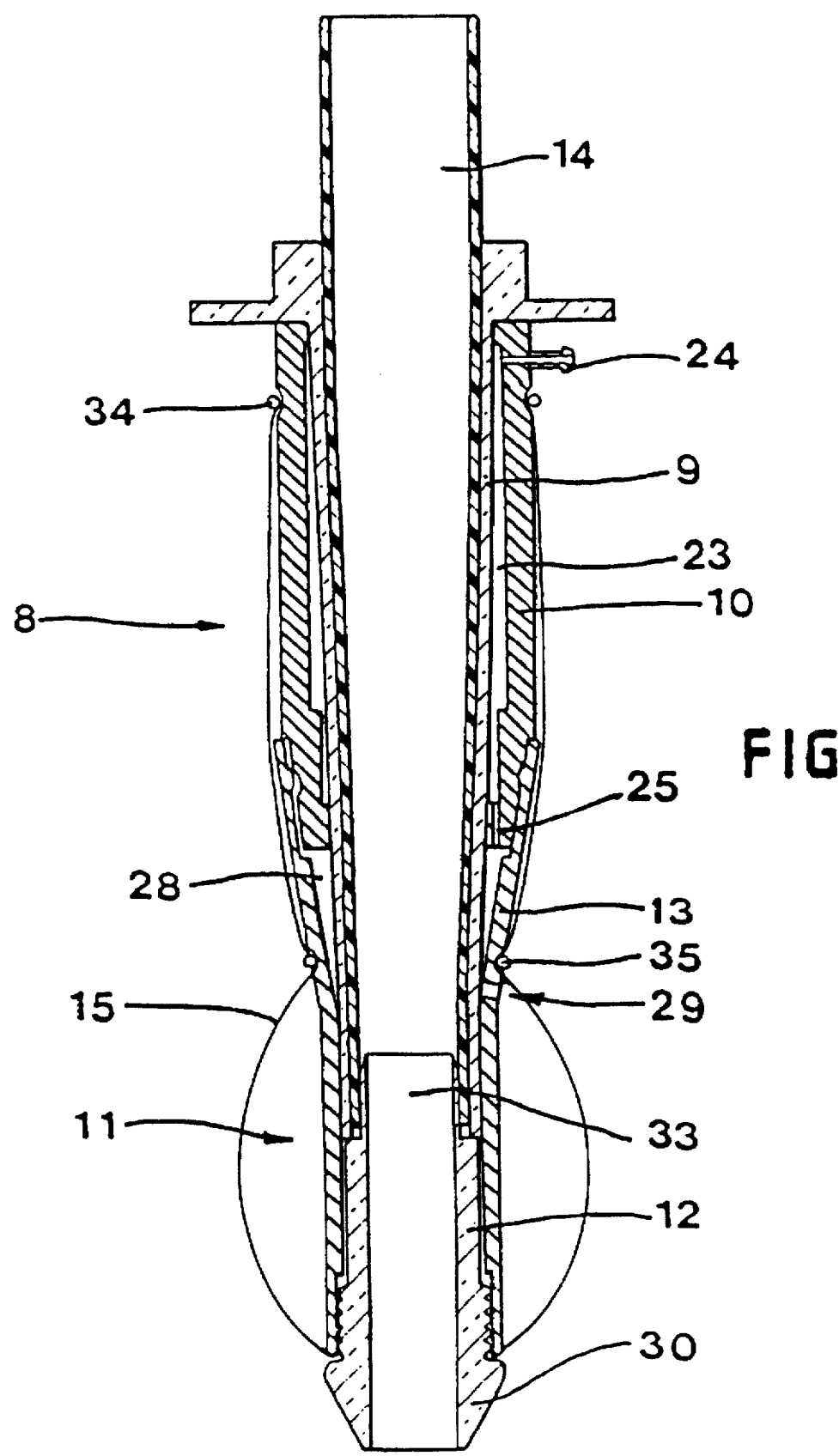
FIG. 2 is a view similar to FIG. 1 showing the speculum with its inflatable element inflated.

Once set up as described above, the speculum is as shown in FIG. 1. It may then be inserted into the vagina. Air is then pumped in through the nipple 24, and flows via the airway 23, transfer port 25, airway 28 and outlet port 29 into the sealed space between the sheath 15 and the outer probe part 13. This inflates the sheath so that it expands as shown in FIG. 2.

The expansion of the sheath dilates the vagina, centralises the speculum therein and, importantly in some instances, seals off the inner end of the vagina.

This last mentioned effect is important because of the growing practice of obtaining cellular material for diagnostic purposes, not by scraping with a spatula but rather by irrigating the vagina and then withdrawing some of the irrigating fluid for examination. Hitherto this has been a somewhat awkward or messy procedure, and is greatly facilitated by temporarily sealing off the upper end of the vagina to prevent fluid leakage external of the speculum.

When inserting the speculum the operator may insert a second, temporary disposable, single use liner tube through the liner 14. That temporary liner reaches to or just beyond the bottom end of the inner probe part 12. It serves to collect any mucus or other matter that may be present, enabling same to be disposed of with the temporary liner when it is withdrawn from the liner 14 immediately before the inspection or operation commences.

In practice the disposable, single use, components of the speculum, namely the probe parts, sheath, 0-ring and liner would be provided in a sterile condition and in a sterile package for assembly to the tubular body by the operator immediately before use. At the end of the procedure all of those parts would be discarded.

Although described above primarily with reference to examination of the vagina, it will be appreciated that speculums according to the invention, but probably modified in respect of the size and shape of their various components to suit the body cavity concerned, may be used quite generally for internal examination of other body cavities, for example the lower bowel, or, for veterinary use, the body cavities of animals.

I claim:

1. A speculum, for use in examining the interior of a body cavity, comprising a tubular body having two ends, a tubular probe adapted to enter said body cavity detachably secured to said tubular body so as to project beyond one of the ends thereof, an inflatable element encircling said probe, and means to inflate said element, and wherein said tubular body and said tubular probe are at least partly made of transparent material to permit light to be transmitted from end to end of said speculum through said transparent material.

2. A speculum according to claim 1 wherein the inflatable element is in the form of a sheath of film covering a length of the probe and sealed to the probe at each end of that length.

3. A speculum according to claim 2 wherein said sheath of film extends as an uninflated skirt beyond one seal so as to at least partly cover said tubular body.

4. A speculum according to claim 2 wherein said means to inflate comprise means to admit gas to a space between the sheath and said length of the probe.

5. A speculum according to claim 1 wherein the other end of said tubular body is adapted for connection to an eyepiece and light source.

6. A speculum according to claim 1 further comprising tubular liner extending through the bore of said tubular body.

7. A speculum according to claim 1 wherein said probe comprises an outer probe part detachably secured to said tubular body and an inner probe part lodged within the bore of said outer probe part.

8. A speculum according to claim 7 wherein the inflatable element is in the form of a sheath of film covering a length of the probe and sealed to the probe at each end of that length, and wherein the seal at one end of that length of probe is effected by virtue of an end portion of the sheath being sandwiched between said outer probe part and said inner probe part.

* * * * *